United States Patent [19]
Morimoto et al.

[11] Patent Number: 6,003,720
[45] Date of Patent: Dec. 21, 1999

[54] DISPOSABLE DENTAL MIXING BOWL

[76] Inventors: Rick H. Morimoto; Patricia T. Morimoto, both of 14932 Merced Cir., Irvine, Calif. 92604

[21] Appl. No.: 09/146,387

[22] Filed: Sep. 2, 1998

[51] Int. Cl.[6] .................................................. B65D 1/44
[52] U.S. Cl. ........................................ 220/608; 220/675
[58] Field of Search ................................. 220/608, 671, 220/675, 574, 659, 658, 657, 656

[56] References Cited

U.S. PATENT DOCUMENTS

| | | |
|---|---|---|
| D. 54,956 | 4/1920 | Reily . |
| D. 112,949 | 1/1939 | Morgan . |
| D. 151,431 | 10/1948 | Cooper . |
| D. 190,878 | 7/1961 | Bradford . |
| D. 199,319 | 10/1964 | Watts . |
| D. 203,340 | 12/1965 | Bolde . |
| D. 237,770 | 11/1975 | Daenen . |
| D. 258,085 | 1/1981 | Porteous . |
| D. 259,011 | 4/1981 | Daenen . |
| D. 287,917 | 1/1987 | Pomroy . |
| D. 313,148 | 12/1990 | de Winter . |
| D. 373,932 | 9/1996 | Onneweer . |
| 2,406,380 | 8/1946 | Johnston, Jr. ............................ 220/671 |
| 3,407,924 | 10/1968 | Lewis . |
| 3,610,586 | 10/1971 | Price . |
| 3,659,825 | 5/1972 | Reiter . |
| 4,166,868 | 9/1979 | Ando et al. . |
| 4,293,080 | 10/1981 | Letica ...................................... 220/659 |
| 4,781,321 | 11/1988 | Koyata et al. ........................... 220/574 |
| 5,415,339 | 5/1995 | Howard .................................... 220/671 |
| 5,709,467 | 1/1998 | Galliano, II . |

*Primary Examiner*—Stephen Castellano
*Attorney, Agent, or Firm*—Ben E. Lofstedt

[57] ABSTRACT

A disposable, thin-wall mixing bowl for dentists used for mixing batches of a combination of liquid and powdered materials used for taking dental impressions of the patient's teeth is described consisting of a bowl, a hollow base, a plurality of longitudinally-arranged, external ribs extending from the base up to just below the rim and a rim having a rounded and beveled portion thereabout.

1 Claim, 2 Drawing Sheets

DISPOSABLE DENTAL MIXING BOWL

BACKGROUND OF THE INVENTION:

1. Field of the Invention

The field of the invention relates to mixing bowls wherein a combination of liquid and powdered materials are mixed, and, more specifically, to disposable, handheld dental mixing bowls.

2. Description of the Prior Art

In the practice of dentistry, dentists must oftentimes mix various materials, such as is required in the formation of artificial stone, plaster, alignate and water, and also in the mixing of certain dental repair material of the two-part type in which a plastic ingredient and a catalyst are employed.

The weights and forces and quantities of such materials involved in a single mixing necessary to achieve a uniformity of mixing of all of the materials and liquids involved, all previously required the use of permanent, relatively staunch and durable reuseable containers. The use of such containers involves considerable initial expense, and requires repeated, time-consuming maintenance, such as cleaning, and sterilizing.

The prior art consists largely of the use of mixing bowls, spoons and spatulas to mix liquid and powdered materials into a paste used for creating impressions of a patient's teeth commonly referred to as dental impressions.

Dentists use alignate which is a salt of alginic acid, such as sodium alginate or magnesium alginate, to prepare castings of their patients' teeth. Alginates possess properties which make them suitable for surgical dressings, dental impression material, and the like. Initially, the alginate is in a dry powder form. To prepare the alginate for such dental applications, the dentist will place a certain amount of the alginate into a bowl and add water. The amount of alginate powder and water required will vary depending upon the brand of alginate used. This precise amount to be mixed with a certain amount of water is information which is generally provided by the manufacturer.

"Alginate" is the term used herein to refer to an irreversible alginate-based hydrocolloid. Several sources of alginate are found commercially which are useful for this purpose. Such sources of alginate are comprised of approximately 12 to 15% sodium alginate which is used as a reactant, approximately 8 to 12% calcium sulfate dihydrate, which is used as a reactant, approximately 2% sodium phosphate or sodium carbonate which is used as a retarder, and approximately 70% reinforcing filler such as diatomaceous earth. Alginate is available commercially under various brand names such as Algiden®, Co-Alginate®, Hydro-Jel®, Jeltrate®, and Supergel®, among others.

The alginate and water mixture must have a pasty gel-like flowable consistency. It cannot be too soupy, nor too dry, and powdery 'pockets' in the mix are unsatisfactory. Thus, the water must be added in exact proportions and then mixed thoroughly to ensure that the water is evenly distributed. This generally entails mixing the alginate in a bowl either with a spatula or by machine. The spatula method is messy and the machine method requires the purchase of a machine. Both methods require clean-up after the mixing is finished. In addition, the spatula method also requires a certain level of skill. The alginate and water must be mixed vigorously to ensure thorough distribution of the water to all the powder in the mixing bowl. However. the mixing must be gentle until the mixture becomes substantially pasty in order to avoid loss of the powder.

After the mixture is formed, the dentist will place in it a mouth-sized preformed impression tray that will then be placed in the patient's mouth to form an imprint of his or her teeth. When the alginate hardens, it can be used to form a casting of the patients' teeth by pouring an alpha modified gypsum or plaster-of-Paris or another similar substance into the imprint.

The traditional dental mixing bowl is formed of rubber and has relatively thick sidewalls and is made to be used over and over again. After mixing the combination of liquid and finely powdered material in the dental mixing bowl, the rubber mixing bowl must be cleaned. Cleaning this rubber bowl is a time consuming job and usually the unused mixed material is flushed down the sink. Oftentimes, the plumbing drain system gets clogged with the mixed dental material requiring a plumber to unclog the drain.

Additionally, the reuse of the rubber bowl creates the continuing risk of the transmittal of infectious diseases due to the lack of being able to fully and completely sanitize the inside surface of the rubber bowl where the mixing of the liquid and the powdered materials takes place.

It is not unusual for a dentist to use the very same rubber dental mixing bowl throughout the dentist's entire working lifetime.

In the past, such may have been an acceptable practice and use of a rubber dental mixing bowl during an era of smaller populations coupled with, regional isolation between various populations over long periods of time, fewer diseases, fewer exotic diseases, such as Hepatitis A, B, and C, Mad-Cow Disease, various strains of virally-caused flus, blood and body fluids transmitted diseases, such as AIDS, tuberculosis, along with fewer encounters with large groups of people. There is no known and acceptable, non-destructive method for sanitizing the traditional rubber dental mixing bowl.

Further, the traditional rubber dental mixing bowl is made to be re-usable and is not considered disposable.

Additionally, the traditional rubber dental mixing bowl has a wall which is formed to be relatively and uniformly thick, with the thickness of the wall defining the degree of manual flexibility of the wall of the bowl during the manual mixing process between the liquid and the powdered materials. The wall of the mixing bowl must be relatively stiff over about a two (2) inch span of wall, and, yet allow for manual manipulation of the wall of the mixing bowl to promote the mixing process as the bowl is rotated by one hand while the other hand is using a spoon-like mixing device.

Examples of the prior art include the following prior art patents:

U.S. Pat. No. D-59,956 relates to a design patent for an individual ice cream container. While this container has the vertically-disposed ribs on the wall about the outside of the body of the bowl, all of the ribs are contiguous rather than spaced-apart as in the inventive product described herein. The ribs are spaced apart to allow the fingers of the user to manipulate the bowl and to rotate it to enhance the mixing process. Additionally, the base or bottom of the bowl is shaped in the form of several hemispherically-shaped knobs instead of the hollow base with a continuous rim thereabout formed as an integral part of the bottom of the bowl and taught by the instant invention disclosed herein.

U.S. Pat. No. D-112,949 relates to the design of a cup. This particular cup design has external, vertically-arranged ribs which are spaced apart, the ribs extend from the bottom of the bowl to the rim of the cup. The ribs in the within described product do not extend from the bottom to the top of the rim as does the cup shown in this patent. Another distinctive difference between the presently disclosed product and the within invention is that the base of the presently disclosed product is within the diameter of the bottom of the bowl.

U.S. Pat. No. D-151,431 relates to the design of a cup having elongated ribbed portions thereon.

U.S. Pat. No. D-190, 878 discloses the design of a shallow pitcher with a laterally extending lipped portion about the rim of the pitcher.

U.S. Pat. No. D-199,319 relates to the design of a drinking tumbler having a plurality of elongated ribbed portions thereabout.

U.S. Pat. No. D-203,340 relates to a design for a "mixing apparatus for dental materials".

U.S. Pat. No. D-237,770 relates to a design for a pitcher which looks very similar to a flower pot.

U.S. Pat. No. D-258,085 discloses a design for an electric dental material mixer. It appears that the traditional rubber mixing cup or bowl is positioned on top of the housing for the electric mixing apparatus.

U.S. Pat. No. D-259,011 teaches a design for a mixing bowl or the like. In addition to the base, this design shows a outwardly extending rimmed portion with a section to be utilized for pouring liquid from the mixing bowl.

U.S. Pat. No. D-287,917 is a design patent for a microwave oven covered dish.

U.S. Pat. No. D-313,148 relates to a design patent covering a bowl with a tabbed portion extending from the rim of bowl for manually gripping the rim of the bowl to hold the bowl during mixing activities.

U.S. Pat. No. D-373, 932 covers a mixing bowl design.

U.S. Pat. No. 3,407,924 relates to a method and package for producing dental molds or molding material. A package unit of a container containing compressed gypsum powder material compressed and sealed is disclosed in this patent along with the method of producing a liquid-gypsum mixture used in dental application. The package serves as the mixing container for the dental model material. The container is disposable.

U.S. Pat. No. 3,610,586 teaches a mixing device for dental products that uses a disposable cup made of plastic.

U.S. Pat. No. 3,659,825 relates to a dish for mixing denture repair materials. An internally-ribbed, relatively thin walled container 12 is used as part of a two part container system as shown and illustrated in FIG. 1. The dish for mixing dental repair material is made from plastic and is intended to be disposed of when the mixing is finished.

U.S. Pat. No. 5,709,467 teaches a device for mixing alginate and may be discarded after use.

The problems associated with the prior art have been solved by creating a disposable dental mixing bowl with a thin wall made of plastic material, along with external ribs to enhance and add structural support and a measured degree of stiffness to the sidewall of the bowl. The plurality of vertically-arranged, externally disposed ribs additionally provide a series of longitudinally arranged, raised portions extending from the base of the bowl to a point adjacent to the rim of the bowl to allow the bowl to be manually rotated while the materials are being mixed. This greatly improves the speed at which such combination of liquid and powdered material can be mixed, combined and rendered uniform. Since the dental mixing bowl is disposable, it is used only once and the bowl, along with the remaining material in the bowl, is simply disposed of by tossing the entire combination, bowl and all, into the trash can. This eliminates the need to wash the materials out of the dental mixing bowl and into the plumbing drain which frequently produces stoppage of the plumbing drain. In summary, not only does the new and unique disposable thin wall plastic mixing bowl eliminate the risk of the transmittal of infectious diseases such as in the case when the prior art rubber mixing bowl is used, but the use of the new bowl also eliminates the usual plumbing blockage problem as well because the bowl is simply tossed into the trash and the remaining mixed materials are not flushed down the plumbing drain as is the procedure when using the prior art rubber, non-disposable dental mixing bowl.

SUMMARY OF THE INVENTIONS AND OBJECTS

Fundamentally, there is described and disclosed herein as the new and novel invention in the form of a new and improved, disposable dental mixing bowl comprising a bowl having a wall forming the side and the bottom of the bowl, the bowl having a open top portion having a rim and a closed bottom portion disposed beneath the rim, a hollow base secured to the bottom of the exterior of the wall of the bowl, a plurality of external ribs secured to the exterior side wall of the bowl, the ribs extending from the base up to a point beneath the rim; and a rounded portion contouring the rim of the bowl. The disposable dental mixing bowl is preferably formed of plastic material with relatively thin and stiff was thereabout, and a plurality of longitudinally arranged, laterally spaced, externally disposed ribbed portions thereon for stiffening the wall of the bowl and for providing a plurality of finger-gripping surfaces thereon for both gripping and rotating the longitudinal wall of the bowl while stirring and mixing the liquid and powder combination in the bowl.

It is an important object of the present invention to provide for an improved mixing bowl construction and design for the mixing of dental materials, such as alginate, and the like, where sufficient quantities of liquid and powder material may be mixed at a single mixing, the unique bowl construction being of a form and structure for stable positioning on a supporting surface during the mixing operation.

It is a further significant feature and object of the within invention to provide for a unique dental mixing bowl to permit the dental mixing bowl to be readily and easily held in the hand of the user to provide enhanced agitation of the mixture to achieve a uniform mixture more quickly and with less effort than previously possible.

Another yet still further object of the instant invention is to provide an improved dental mixing bowl wherein the maintenance and labor involved in cleaning and sterilization is virtually eliminated.

It is one primary and important object of the instant invention to provide a new and improved plastic, disposable dental mixing bowl.

A yet still further primary object and feature of the present invention is to provide an improve dental mixing bowl construction of the type described herein wherein a relatively inexpensive dental mixing bowl is provided without the need or use of other supporting structures wherein the mixing operation can occur in which the bowl is extremely inexpensive so as to allow the dental mixing bowl to be discarded after but single use.

Another important and primary feature of the present invention is to provide a thin-wall mixing bowl for mixing alginate for use for dental impression purposes.

It is another object of the instant invention to sanitarily prepare an alginate and water mixture.

Another significant and important object of the within invention is to provide a means of completely and uniformly mix alginate with water.

A yet still further and primary object of the present invention is to make the preparation of alginate and water mixture more efficient.

It is another primary object and feature of the instant invention to provide a means for efficiently mixing alginate and water to eliminate dry powder portions, bubbles and voids in the mixture.

Another important feature and object of the invention disclosed and described herein is to provide an improved dental mixing bowl construction wherein in a single structure is combined the features of what formerly required two (2) separate structures in the form of a bowl and a metal supporting structure in order to effectively achieve both rigidity and enhanced agitation in the mixing operation.

Another important feature of the within invention is to reduce the probability of introducing contagions into the mixture by the use of a non-reuseable dental mixing bowl.

It is a yet still further object of the invention to eliminate the time and effort necessary for the cleanup of the bowl after the mixing process and use of the alginate/water mixture.

Other objects of the present invention will become apparent upon reading the following specification and referring to the accompanying drawings, which form a material part of this disclosure.

The invention accordingly consists in the features of construction, combinations of elements, and arrangements of parts, which will be exemplified in the construction hereinafter described, and of which the scope will be indicated by the appended claims.

DETAILED DESCRIPTION OF THE PREFERRED EMBODIMENTS OF THE INVENTION

Figure 1:
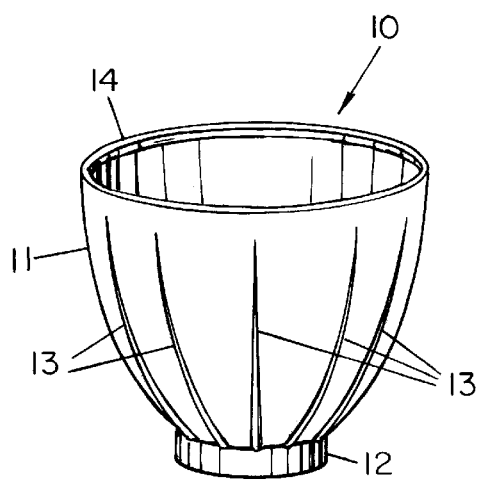
FIG. 1 is an perspective view of the present invention referred to as a disposable dental mixing bowl.
Figure 2:
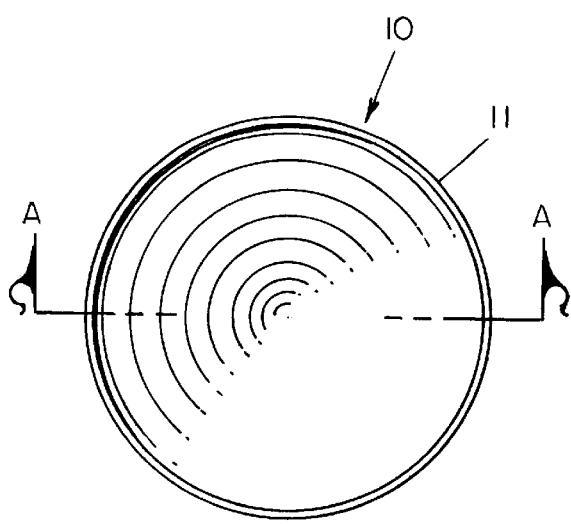
FIG. 2 is a top view of the instant invention.
Figure 3:
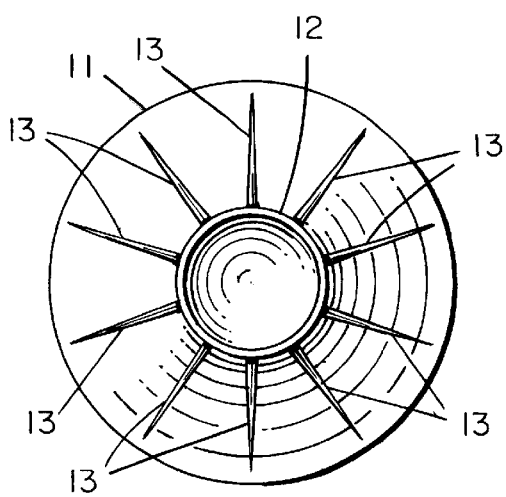
FIG. 3 is a bottom view of the new and unique invention disclosed herein.
Figure 5:
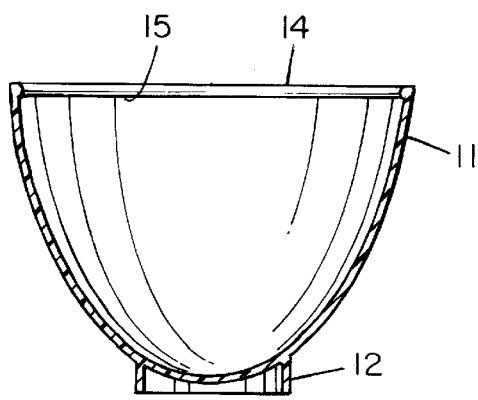
FIG. 5 is an enlarged section taken along Plane A—A of FIG. 1.
Figure 4:
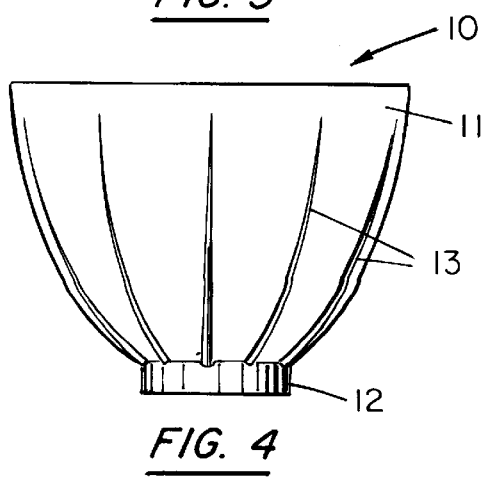
FIG. 4 is a side elevational view of the disposable dental mixing bowl described herein.

With continued reference now to all of the Drawings herein, there is fundamentally shown the present invention disclosed and described herein which is referred to as an improved disposable dental mixing bowl and is generally indicated at 10. With specific reference now more particularly to FIGS. 1 through 4, inclusive, there is a shown a new and unique disposable dental mixing bowl, generally indicated at 10, comprising a bowl 11, a base 12, a plurality of external ribs 13, and a rim 14 having a rounded and beveled portion 15, the angle of the bevel tapering from the outside of the rim 14 and downwardly towards the inside of the bowl 11.

The preferred material used to form the disposable dental mixing bowl 11 is plastic. Among such suitable plastic materials is the plastic material called polystryene,

Prior Art Non-Disposable Dental Mixing Bowl

Figure 6:
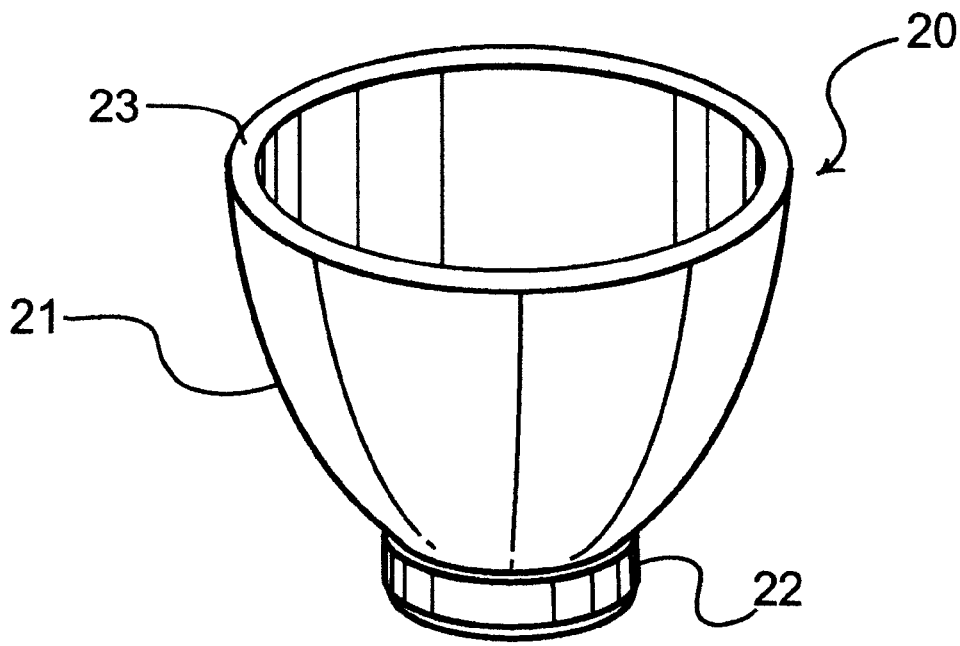
FIG. 6 is a perspective view of the rubber dental mixing bowl found in the prior art.
Figure 7:
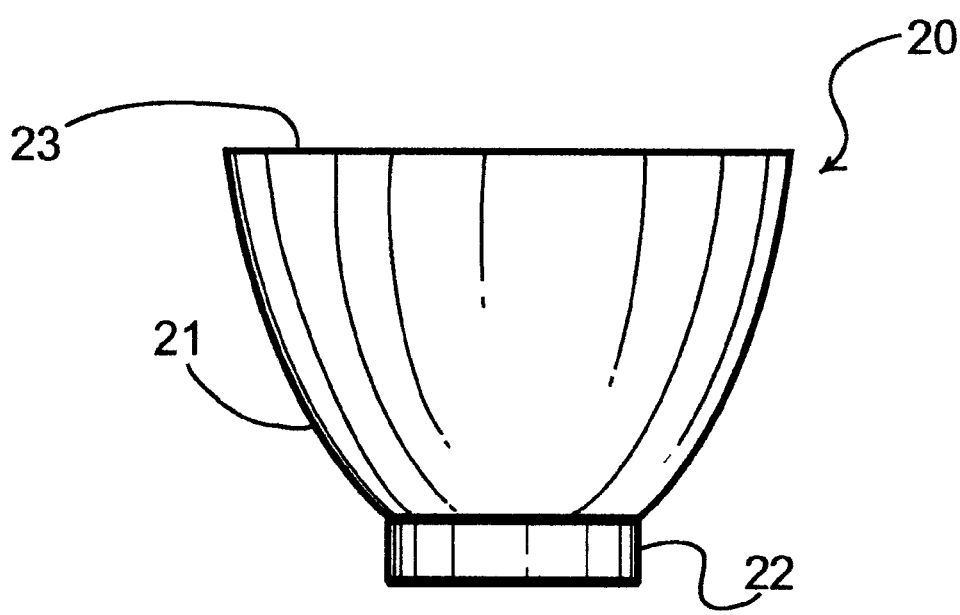
FIG. 7 is a side elevational view of the rubber dental mixing bowl found in the prior art.

With special reference now to both FIGS. 6 and 7, there is shown and illustrated the prior art dental mixing bowl generally indicated at 20. This one such example is manufactured under the tradename HYGIENIC FLEXIBOLE and is made of a rubber compound designed to "last a lifetime". As noted in the drawings of the prior art dental mixing bowl 20, the wall 21 of the rubber dental mixing bowl 20 is relatively thick, being, in the case of the HYGIENIC FLEXIBOLE product referred to herein by way of example, a nominal three sixteenths ($3/16$) of an inch thick. The height of this rubber dental mixing bowl 20 measured from the outermost extremity of the bottom of the solid base 22 and the top of the rim 23, is three and three-quarters ($3\frac{3}{4}$) inches and it incorporates a solid base 22 measuring two and one-sixteenth ($2\frac{1}{16}$) inches in diameter and from one-quarter ($\frac{1}{4}$) to three-eighths ($\frac{3}{8}$) of an inch thick. The rim 23 of the bowl measures four and seven-eighths ($4\frac{7}{8}$) inches in diameter. The rim 23 is flat and is neither beveled or rounded. The wall 21 of the rubber dental mixing bowl 20 does not incorporate any external ribs. The base 22 is solid and not hollowed out. Due to the relatively thick walled construction of the prior art dental being formed of a rubber compound, the weight of the prior art dental mixing bowl 20 is much heavier in weight than the new disposable dental mixing bowl 10 described herein.

Operation and use of the Improved Disposable Dental Mixing Bowl

Turning now to the invention 10 described and disclosed herein, one of the great improvements provided by the new and improved dental mixing bowl 10 of the type and character disclosed herein is that it is both sanitary and hygienic to reduce significantly the possibility of the transmittal of diseases from one person to another through the use of a reuseable, non-disposable, dental mixing bowl 20 formed of rubber which is not, and cannot be, sanitized inbetween the mixing of one dental compound batch for one patient and mixing another batch for another patient.

While many plastic compounds are suitable for use in the formation of the within described improved dental mixing bowl 10, one such suitable plastic compound is polystyrene. Polystyrene is sanitary and non-reactive with the compounds being mixed for dental use. Polystyrene is readily moldable into complex shapes by conventional injection molding techniques, and readily meets the durable standards for the use intended. Further, polystyrene is moldable into very thin-walled structures allowing for a minimum of waste when the improved dental mixing bowl 10 is disposed of following mixing of the dental compounds.

The longitudinal wall 11 of the new disposable mixing bowl 10 has a plurality of external ribs 13 extending from the base 12 up to near the rim 14 of the bowl 10. These ribs 13 are spaced apart equidistantly to provide space to allow for finger-gripping of the surfaces inbetween the ribs 13 so that the mixing bowl 10 can be manually rotated in a positive, consistent fashion, while the dentist or lab technician mixes the powder with the liquid to create dental impression material. Such mixed material is used for creating a mold for a patient's teeth and also for casting an identical replica of the patient's teeth. The manual rotation of the bowl 10 is important to greatly decrease the amount of time required to mix the dry powders and the liquids and to also ensure that the powder is fully mixed with the liquid with no un-mixed, powder only-portions remaining or bubbles or voids in the mixed combination of materials.

The rim 14 contains a rounded and beveled surface at 15. This rounded and beveled surface 15 acts as one of the reference points for the fingers during the process of rotating the bowl 10 during mixing. The other reference points are created by the terminus of each of the ribs 13 on the body of the bowl 10. If the fingers should become positioned between the terminus of the ribs 13 on the body of the bowl 10 and the ends of the rounded and beveled surface of the rim 15, the fingers detect the lack of the raised ribs 13 and determine that the fingers are too close for optimal use and are given an early warning opportunity to return to optimal use. Additionally, the plastic material forming the wall of the bowl 10 is so relatively thin that the failure to provide a rounded and beveled surface would expose the user of the bowl 10 to risk of cutting his or her fingers. Still further, the incorporation of a rounded and beveled surface 15 about the rim 14 acts to rigidize the rim 14 against excessive bending during the process of mixing which, should such excessive bending occur, the edge of the rim 14 to fracture resulting in a sharp, knife-like edge thereby creating an unnecessary risk of harm to the user. Preferably, the thickness of the rounded and beveled surface 15 about the rim 14 should be no greater than twice the thickness of the wall of the bowl 10.

In use and in application, the ribs 13 are arranged in equidistant, spaced apart relationship to each other. The thickness of the material forming the ribs 13 is larger at the base 12 of the bowl 11 and tapers down in thickness where it terminates prior to reaching the rim 14. Such arrangement provides for a stiffer base or bottom portion of the bowl 10 and a more flexible area between the terminus of the rib 13 and the rim 14.

We have discovered that in the practicing of our invention herein that the best mode involves a bowl formed of polystyrene plastic material, wherein the diameter of the essentially circular rim of the bowl is four (4) and five-eighths (⅝) inches, that the overall height of the bowl including the thickness of the base is three (3) and one-half (½) inches, that the diameter of the essentially circular base is one (1) and three-quarters (¾) inches, that the thickness of the base is three-eighths (⅜) inches high, that the number of exteriorly-projecting ribs is ten (10) in number, that the space between the ribs at the terminus of the ribs with the top of the base is from about three-eighths (⅜) to seven-sixteenths (7/16) inches, that the width of each rib at its terminus with the top of the base is one-eighth (⅛) inch, that the opposite end of each rib stops at about one-half (½) inch from the top of the rim of the entrance of the bowl, and the wall thickness is about one thirty-second (1/32) inches thick.

The prior art dental mixing bowl 20 formed of a rubber compound uses a wall 21 having a thickness of 0.187 inches. The disposable dental mixing bowl 10 disclosed herein uses a wall 11 which is only 0.020 inches thick, which is nearly ten (10) times thinner than the wall of the prior art dental mixing bowl 20.

Additionally, the ratio of the height to wall thickness for the prior art dental mixing bowl 20 is 3.75/0.187 or 20. The ratio of the height to wall thickness for the within disclosed disposable dental mixing bowl 11 is 3.50/0.020 or 175. In comparing the two ratios, the new disposable dental mixing bowl 11 is 175/20 or 8.75 times greater than the height to wall thickness ratio of the prior art non-disposable, rubber compound dental mixing bowl.

The prior art non-disposable, rubber compound dental mixing bowl 20 when rotated by hand, the fingers and thumb are frictionally engaged with the wall 21 of the bowl 20 sufficient, in general, to allow the bowl 20 to be rotated by the fingers. However, there is some slippage involved between the fingers and the rubber material forming the bowl 20, and, of course, such slippage measurably reduces the number of degrees of rotation and the speed at which the bowl 20 is rotated. Such measurable variations in the amount of rotation and the speed of rotation has a major effect on the speed of mixing and the time necessary to effectuate a complete mix of the liquid and the powdered material.

From the foregoing, it can be seen that there has been provided an improved disposable dental mixing bowl 10 which affords great flexibility, convenience and vastly improved sanitation over the use of the prior art rubber dental mixing bowl 20.

While the basic principle of this invention has been herein illustrated along with the embodiments shown, it will be appreciated by those skilled in the art that variations in the disclosed arrangement, both as to its details and the organization of such details, may be made without departing from the spirit and scope thereof. Accordingly, it is intended that the foregoing disclosure and the showings made in the drawings will be considered only as illustrative of the principles of the invention, and not construed in a limiting sense.

What we claim as our invention is:

1. A disposable dental mixing bowl comprising:

(a) a bowl having a wall forming the side and the bottom of the bowl, the bowl having a open top portion having rim and a closed bottom portion disposed beneath the rim, wherein the rim of the bowl is an essentially circular rim of about four and five-eighths inches in diameter;

(b) a hollow base secured to the bottom of the exterior of the wall of the bowl an hollow base positioned on the centerline of the circular rim and measuring about one and three-quarters inches in diameter and having a height of about three-eighths of an inch, and an overall vertical height from the bottom of the base to the top of the rim measuring about three and one-half inches;

(c) raised means formed as a integral part of the wall of the bowl and longitudinally arranged from the top of the base to below the rim to act as a means for manually gripping the exteriorly-facing wall of the bowl for rotational manipulation of the bowl; and (d) means for rigidizing the rim of the bowl to prevent excessive bending of the rim during manual mixing of the dental materials.

* * * * *